(12) United States Patent
Hagland

(10) Patent No.: US 10,413,354 B2
(45) Date of Patent: Sep. 17, 2019

(54) END EFFECTOR FOR ELECTROSURGICAL INSTRUMENT

(71) Applicant: GYRUS MEDICAL LIMITED, St Mellons, Cardiff (GB)

(72) Inventor: Michael John Hagland, Caerwent (GB)

(73) Assignee: GYRUS MEDICAL LIMITED, St Mellons, Cardiff (GB)

( * ) Notice: Subject to any disclaimer, the term of this patent is extended or adjusted under 35 U.S.C. 154(b) by 580 days.

(21) Appl. No.: 15/044,807

(22) Filed: Feb. 16, 2016

(65) Prior Publication Data
US 2016/0235473 A1 Aug. 18, 2016

(30) Foreign Application Priority Data
Feb. 13, 2015 (GB) .................................. 1502469.8

(51) Int. Cl.
*A61B 18/14* (2006.01)
*A61B 18/00* (2006.01)
(Continued)

(52) U.S. Cl.
CPC ...... *A61B 18/1445* (2013.01); *A61B 18/1442* (2013.01); *A61B 17/295* (2013.01);
(Continued)

(58) Field of Classification Search
CPC ............ A61B 18/1445; A61B 18/1442; A61B 18/085; A61B 2090/034; A61B 2090/035;
(Continued)

(56) References Cited

U.S. PATENT DOCUMENTS 5,361,583 A * 11/1994 Huitema ................ A61B 17/00 60/413
7,473,253 B2 1/2009 Dycus et al.
(Continued)

FOREIGN PATENT DOCUMENTS

DE 10 2008 018 614 A1 10/2009
WO 2012/156400 A1 11/2012

OTHER PUBLICATIONS

Jul. 15, 2015 Search Report issued in British Patent Application No. GB1502469.8.

*Primary Examiner* — Daniel W Fowler
*Assistant Examiner* — Christine A Dedoulis
(74) *Attorney, Agent, or Firm* — Oliff PLC

(57) ABSTRACT

An end effector for an electrosurgical instrument includes a pair of opposing first and second jaw members (2), (3), movable between an open position in which the jaw members are disposed in a spaced relation relative to one another, and a closed position in which the jaw members cooperate to grasp tissue therebetween. One or more spring members (15), (16), (17), (18), (19) are connected between the first and second jaw members (2), (3), such that moving the jaw members from their open position to their closed position causes the one or more spring members to compress. The one or more spring members have a fully compressed condition such that when in their fully compressed condition they form stop members to maintain the first and second jaw members (2), (3), at a predetermined spacing one from the other when in their closed position.

15 Claims, 4 Drawing Sheets

US 10,413,354 B2

Page 2

(51) Int. Cl.
*A61B 90/00* (2016.01)
*A61B 17/295* (2006.01)

(52) U.S. Cl.
CPC ............... *A61B 2018/0063* (2013.01); *A61B 2018/00083* (2013.01); *A61B 2018/1452* (2013.01); *A61B 2018/1455* (2013.01); *A61B 2090/034* (2016.02); *A61B 2090/035* (2016.02)

(58) Field of Classification Search
CPC .. A61B 2018/00083; A61B 2018/0063; A61B 2018/1452; A61B 2018/1455; A61B 17/1606; A61B 17/28; A61B 17/29
USPC .... 605/52; 606/51, 205, 206, 207, 208, 209, 606/52
See application file for complete search history.

(56) References Cited

U.S. PATENT DOCUMENTS

| | | |
|---|---|---|
| 8,241,284 B2 | 8/2012 | Dycus et al. |
| 2010/0057084 A1 | 3/2010 | Hanna |
| 2013/0079774 A1* | 3/2013 | Whitney ............ A61B 18/1445 606/52 |
| 2013/0150842 A1* | 6/2013 | Nau, Jr. ............ A61B 18/1445 606/13 |
| 2014/0246474 A1* | 9/2014 | Hall ................ A61B 17/07207 227/175.1 |
| 2014/0276732 A1 | 9/2014 | Strobl et al. |
| 2015/0282866 A1* | 10/2015 | Rothweiler ...... A61B 17/07207 606/51 |
| 2016/0228186 A1* | 8/2016 | Hancock ............ A61B 18/1815 |

* cited by examiner

END EFFECTOR FOR ELECTROSURGICAL INSTRUMENT

TECHNICAL FIELD

Embodiments of this invention relate to an end effector for an electrosurgical instrument, and to an electrosurgical instrument for sealing tissue. Such systems are commonly used for the treatment of tissue in surgical intervention, most commonly in "keyhole" or minimally invasive surgery, but also in "open" surgery.

BACKGROUND TO THE INVENTION AND PRIOR ART

It is known to provide an electrosurgical instrument in which the sealing of tissue is effected by means of a pair of jaw elements. U.S. Pat. Nos. 7,473,253 & 8,241,284 are two examples of this kind of instrument. These two patents describe the provision of one or more non-conductive stop members, in order to regulate the spacing between the jaws when tissue is held therebetween.

SUMMARY OF THE INVENTION

Embodiments of the present invention attempt to provide an improvement to an arrangement instrument such as described above.

Accordingly, an end effector for an electrosurgical instrument is provided, the end effector comprising a pair of opposing first and second jaw members, at least one of the jaw members being pivotable relative to the other between a first open position in which the jaw members are disposed in a spaced relation relative to one another, and a second closed position in which the jaw members cooperate to grasp tissue therebetween, the jaw members being capable of being connected to a source of electrical energy such that the jaw members are capable of conducting energy through tissue held therebetween to effect a tissue seal, the end effector including one or more spring members connected between the first and second jaw members such that moving the jaw members from their open position to their closed position causes the one or more spring members to compress, the one or more spring members having a fully compressed condition such that when in their fully compressed condition the one or more spring members form stop members to maintain the first and second jaw members at a predetermined spacing one from the other when in their closed position.

The one or more spring members therefore act not only as a way of regulating the resistance of the jaws to closure by the user, but also as a stop member to regulate the spacing between the jaws when they are in their closed position. Conveniently, the first and second jaw members are each pivotable with respect to each other about a common pivot. The end effector conceivably includes a single spring member located adjacent the pivot, or alternatively two spring members located one on either side of the longitudinal axis of the end effector. The jaw members typically include a sealing area in which the tissue is grasped, the sealing area often being provided with electrodes in the form of shims attached to the jaw members. The one or more spring members are preferably located outside the sealing area of the jaw members, such that they do not come into contact with tissue grasped between the jaws.

Even though the one or more spring members are located away from the main tissue grasping area, they are conveniently electrically insulating. Typically, they are formed of an electrically insulating material, such as from a polymer material. Alternatively, the one or more spring members are formed of a metallic material coated with an electrically insulating material.

The one or more spring members are preferably constrained by locating means present on the first and second jaw members. In this way, the one or more spring members are held in position between the jaws in a secure fashion. Conveniently, the locating means comprises recesses present on the first and second jaw members. The one or more spring members are located in the recesses to secure them in position. Alternatively or additionally, the locating means typically comprises location posts present on the first and second jaw members.

According to a first convenient arrangement, the one or more spring members comprise coil springs. Alternatively, the one or more spring members comprise disc springs, or conceivably even leaf springs. Whichever springs are employed, the one or more spring members provide a stop mechanism when they are in their fully compressed condition.

Embodiments of the invention further reside in a surgical instrument comprising;
   i) a handle,
   ii) an elongate shaft attached to the handle,
   iii) an end effector located at the distal end of the shaft, the end effector comprising a pair of opposing first and second jaw members, at least one of the jaw members being pivotable relative to the other between a first open position in which the jaw members are disposed in a spaced relation relative to one another, and a second closed position in which the jaw members cooperate to grasp tissue therebetween,
   iv) first and second connections by which the jaw members can be connected to a source of electrical energy such that the jaw members are capable of conducting energy through tissue held therebetween to effect a tissue seal,
   v) an actuation mechanism associated with the handle for moving the jaw members between their open and closed positions,
     the end effector including one or more spring members connected between the first and second jaw members such that moving the jaw members from their open position to their closed position causes the one or more spring members to compress, the one or more spring members having a fully compressed condition such that when in their fully compressed condition the one or more spring members form stop members to maintain the first and second jaw members at a predetermined spacing one from the other when in their closed position.

The instrument conveniently further includes a cutting blade actuable to cut tissue grasped between the first and second jaw members. Typically, the cutting blade is a mechanical cutting blade mounted such that it can be advanced along the longitudinal axis of the end effector. Alternatively or additionally, the cutting blade is conceivably an electrosurgical electrode selectively connected to a source of electrosurgical energy. Whichever type of cutting blade is employed, the instrument also preferably includes a second actuation mechanism associated with the handle, the second actuation mechanism being actuable to reciprocate the cutting blade longitudinally with respect to the first and second jaw members.

DESCRIPTION OF THE FIGURES

Embodiments of the invention will now be further described, by way of example only, with reference to the accompanying drawings, in which.

DESCRIPTION OF THE EMBODIMENTS

Figure 1:
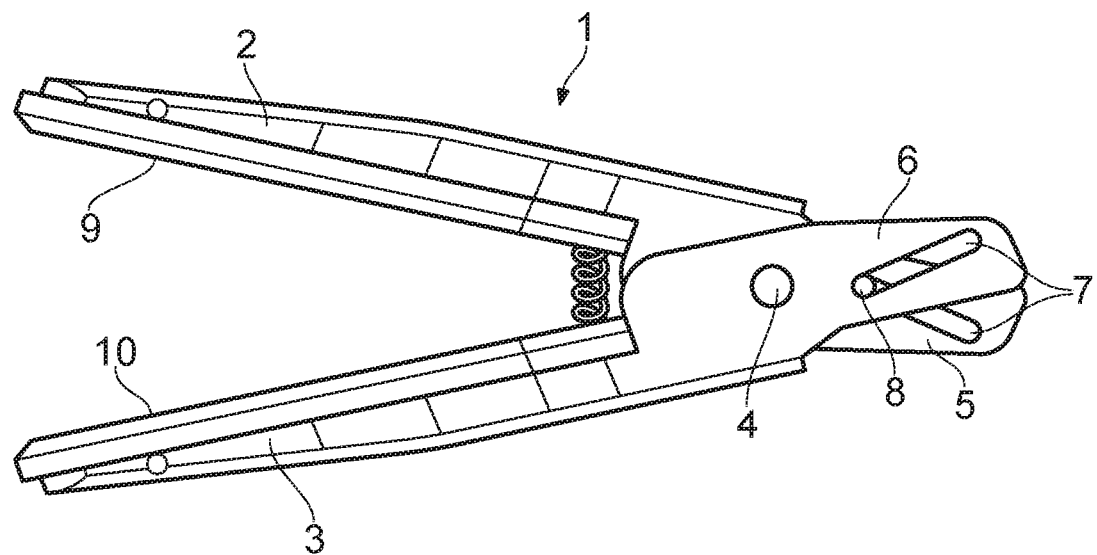
FIG. 1 is a schematic side view of an end effector in accordance with the a first embodiment of the present invention.
Figure 2:
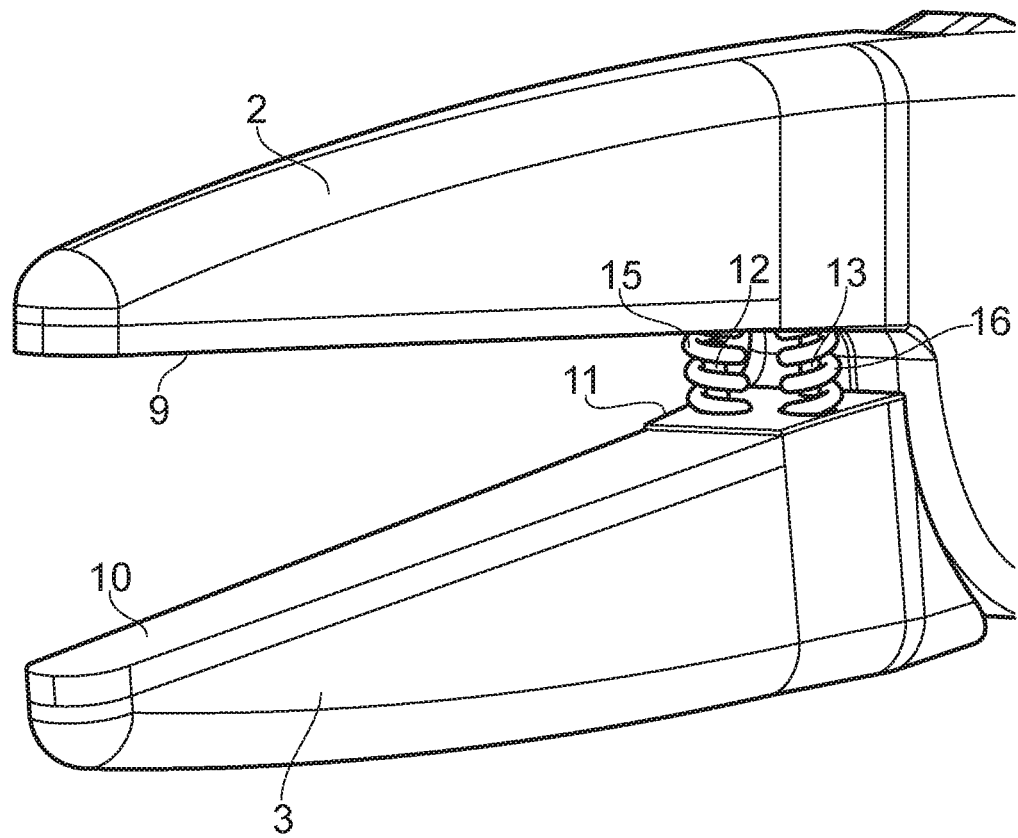
FIG. 2 is an enlarged perspective view of a part of the end effector of FIG. 1.
Figure 3:
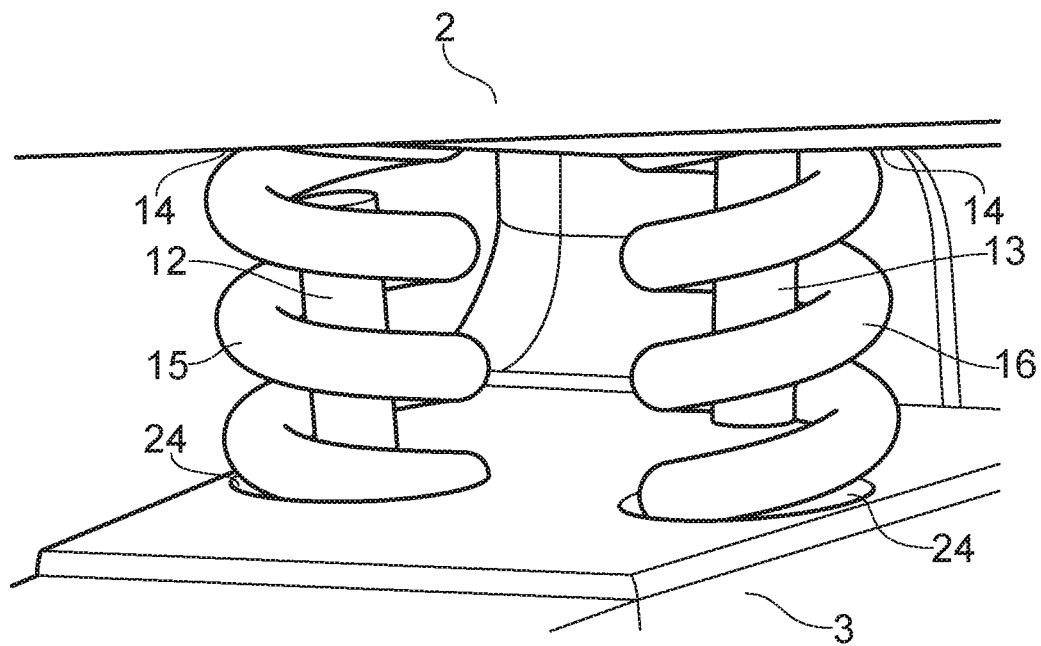
FIG. 3 is a further enlarged perspective view of a part of the end effector of FIG. 1.

Referring to FIGS. 1 to 3, an end effector shown generally at 1 comprises an upper jaw 2 pivotably connected to a lower jaw 3 about a pivot 4. Flanges 5 are present at the proximal end of upper jaw 2, while flanges 6 are present at the proximal end of lower jaw 3. The flanges 5 & 6 each have slots 7 through which a drive pin 8 extends, such that proximal and distal movement of the drive pin 8 (by means of a drive mechanism (not shown)) causes the jaws 2 & 3 to pivot between open and closed positions.

A metallic shim 9 is present on the inward face of upper jaw 2, while a metallic shim 10 is present on the inward face of lower jaw 3. When the jaws 2 & 3 pivot into their closed position, the metallic shims 9 & 10 come into close proximity one with the other, in order to grasp tissue (not shown) therebetween.

Proximal of the shims 9 & 10 and adjacent the area where the jaw members converge is an area 11 in which is provided first and second locating posts 12 & 13. Post 12 is attached to the lower jaw 3, and extends towards the upper jaw 2, stopping short of the upper jaw. Post 13 is conversely attached to the upper jaw 3, and extends towards the lower jaw 3, stopping short of the lower jaw. The posts 12 & 13 are located in recesses 14 & 24 (see FIG. 3), two recesses 14 being present in the upper jaw 2 while two recesses 24 are present in the lower jaw 3. Located around the post 12 is a coil spring 15, while coil spring 16 is located around post 13. Each end of the coil springs 15, 16 is received within one of the recesses 14 & 24, so that, between the posts 12 & 13 and the recesses 14 & 24, the coil springs 15 & 16 are constrained to lie between the upper jaw 2 and the lower jaw 3.

As the jaw members 2 & 3 pivot from their open position towards their closed position, the coil springs 15 & 16 start to become compressed, thereby providing a resistance against the closure of the jaws. However, the structure of the coil springs is selected such that the resistance is relatively easy to overcome, and merely provides a "feel" for the closure of the jaws rather than a serious impediment. Once the jaws 2 & 3 start to approach their closed position, the coil springs 15 & 16 become fully compressed, with adjacent turns of the coil coming into contact with one another to form a closed tube structure. In this condition, the coil springs form a rigid structure between the jaws 2 & 3, with the springs contacting the base of the recesses 14 & 24 at each end. The closed springs therefore form a rigid stop member holding the jaws 2 & 3 apart by a predetermined distance, preferably between about 25 µm to about 350 µm (0.001 inches to about 0.014 inches). This jaw separation helps to ensure that tissue grasped between the jaws is sealed effectively, when an electrosurgical coagulating voltage is passed between the jaws.

Figure 4:
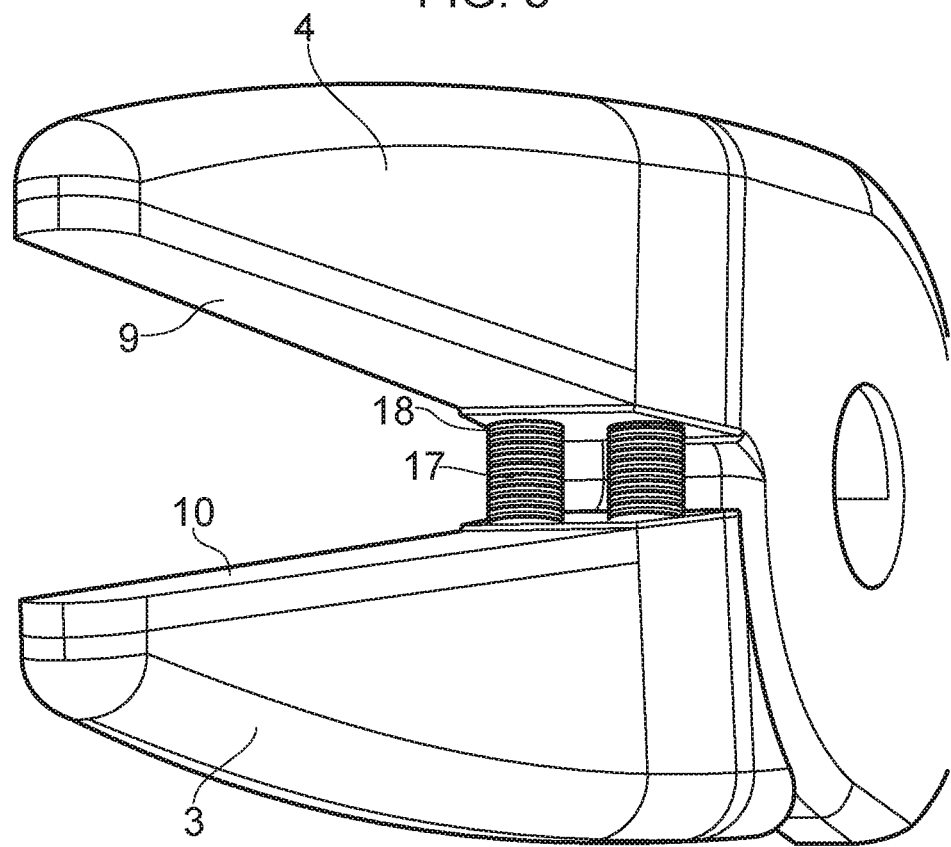
FIG. 4 is a schematic perspective view of an end effector in accordance with an alternative embodiment of the present invention.
Figure 5:
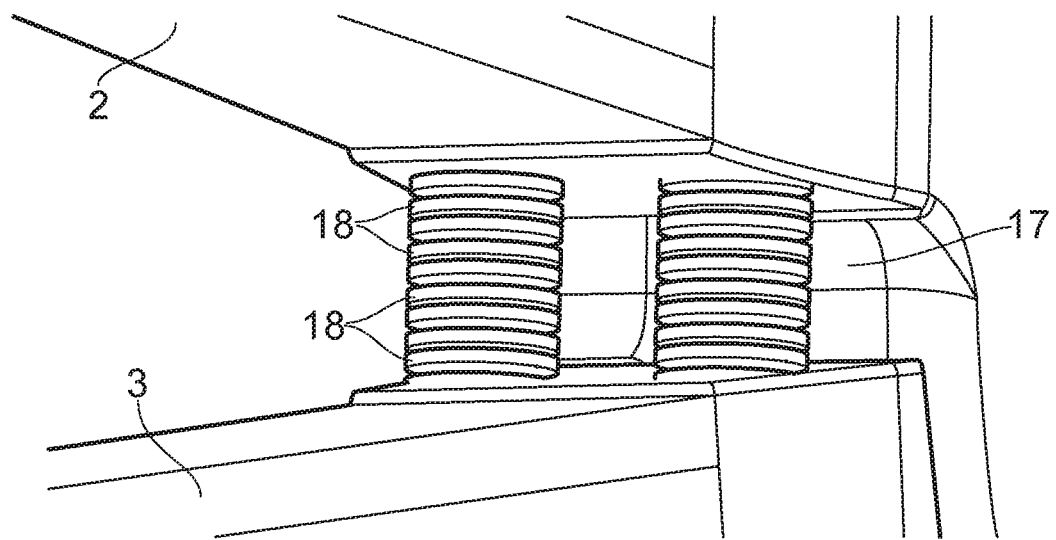
FIG. 5 is an enlarged perspective view of a part of the end effector of FIG. 4.

FIGS. 4 & 5 show an alternative arrangement, in which the coil springs 15 & 16 are replaced with a plurality of disc springs 17. The disc springs 17 each comprise a stack of discs 18, mounted on the posts 12 & 13 are previously described. Each of the discs 18 is compressible from an uncompressed to a compressed condition, as the jaws 2 & 3 are pivoted from their open position into their closed position. As the jaws approach their closed position, the disc springs reach their maximum compression and form a rigid structure incapable of being compressed further. At this point the disc springs 17 form stop members capable of maintaining the minimum separation between the jaw members desired for tissue sealing.

Figure 6:
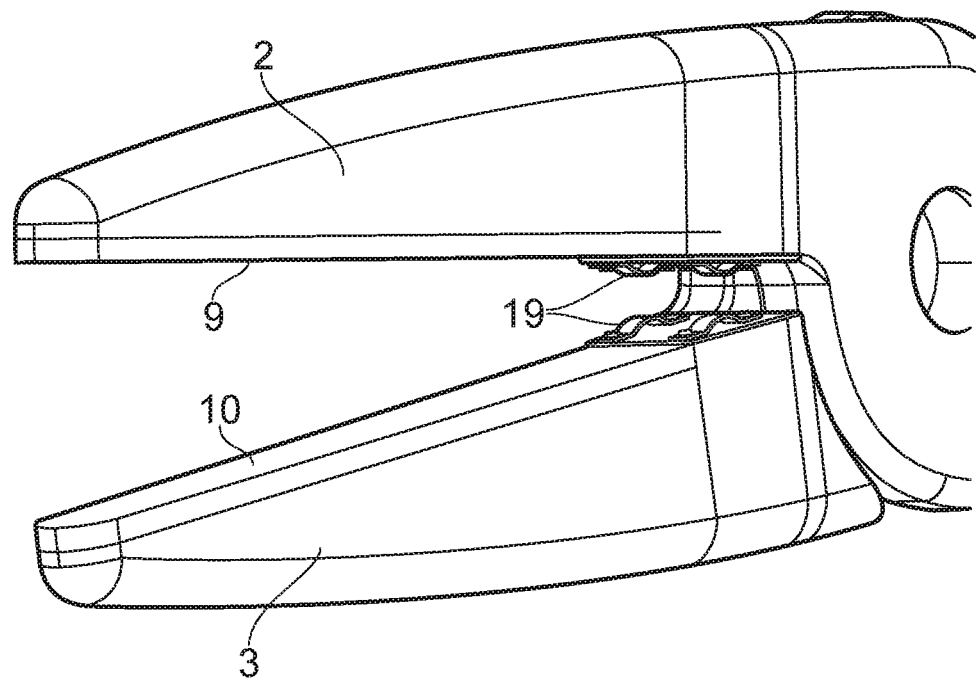
FIG. 6 is a schematic perspective view of an end effector in accordance with a further embodiment of the present invention.
Figure 7:
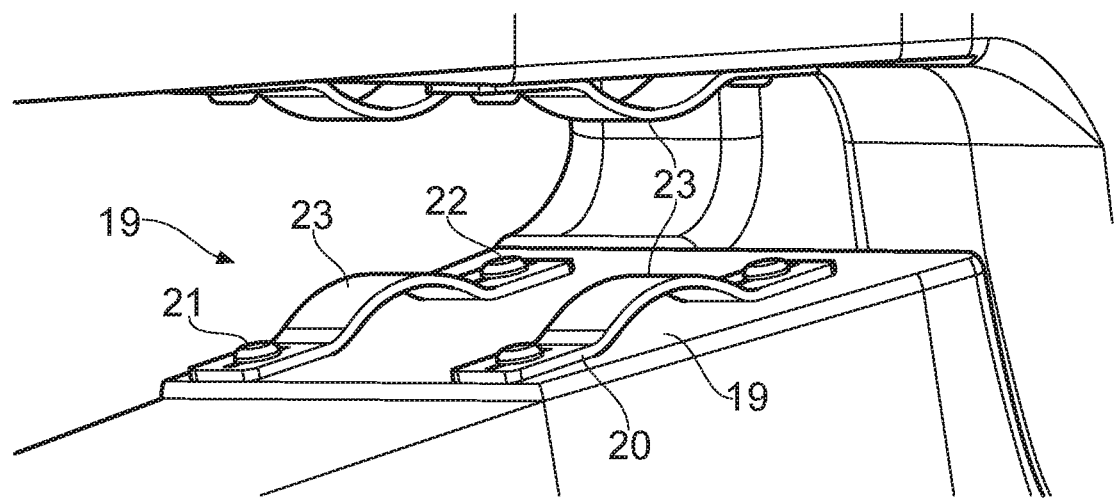
FIG. 7 is an enlarged perspective view of a part of the end effector of FIG. 6.

FIGS. 6 & 7 show a further arrangement, in which leaf springs 19 are provided on each of the jaws. As shown in FIG. 7, each leaf spring comprises a metallic strip 20, secured to the jaw at fixing locations 21 & 22, and having a raised bowed section 23 therebetween. Each of the fixing locations 21 & 22 allows for the sliding movement of the strip 20 either before being fixed in position or even allowing for some sliding movement as the strip is compressed. Two such leaf spring elements are present on the upper jaw 2, and two on the lower jaw 3, each pair disposed in opposite corresponding alignment such that the bowed sections 23 of each leaf spring contact one another as the jaws pivot towards their closed position. When the jaws start to close, the bowed sections 23 flex one against the other to provide a controlled resistive force against the closure. When the bowed sections 23 have reached their maximum deformation, the leaf springs form a rigid structure resisting further compression and forming stop members to regulate the spacing between the jaws 2 & 3.

Whichever arrangement is employed, the provision of spring members not only provides a controlled resistance to the closure of the jaws, but also constitutes stop members regulating the jaw spacing when the spring members are in their fully compressed position. Whether the spring members are coil springs (as in FIGS. 1 to 3), disc springs (as in FIGS. 4 & 5) or leaf springs (as in FIGS. 6 & 7), they are typically formed of an electrically insulating material, such as a polymer material, or formed of a metallic material coated with an electrically insulating material such as polymer. This means that the spring members will not conduct electrosurgical energy to tissue grasped between the jaws, or cause shorting therebetween. In other embodiments the spring members need not actually also provide a positive spring force acting to force the jaws open when the user releases the closure pressure, as long as a controlled reactive resistance to the user pressure to close the jaws is provided. For example, damper type arrangements (for example a heavily damped spring) may be used that provide a reaction against the applied user force to give the controlled resistance to the closure of the jaws, without providing an opening force when the user pressure is released, and which also stop out at the desired jaw spacing when the jaws are fully closed.

The invention claimed is:

1. An end effector for a surgical instrument, the end effector comprising:

a pair of opposing first and second jaw members, at least one of the first jaw member and the second jaw member being pivotable relative to the other one of the first jaw member and the second jaw member between (i) a first open position in which the first jaw member and the second jaw member are disposed in spaced relation relative to one another, and (ii) a second closed position in which the first jaw member and the second jaw member cooperate to grasp tissue therebetween, the first jaw member and the second jaw member being configured to be connected to a source of electrical energy such that the first jaw member and the second jaw member conduct energy through the tissue held therebetween to effect a tissue seal; and at least one spring member connected between the first jaw member and the second jaw member, the first jaw member and the second jaw member moving from the open position to the closed position causing the at least one spring member to compress, the at least one spring member having a fully compressed condition in the closed position, the at least one spring member forming a stop member when the at least one spring member is in the fully compressed condition, the stop member maintaining a predetermined gap distal of the stop member between the first jaw member and the second jaw member along a length of the first jaw member and the second jaw member, when the first jaw member and the second jaw member are in the closed position.

2. The end effector according to claim 1, wherein the first jaw member and the second jaw member are each pivotable with respect to each other about a common pivot.

3. The end effector according to claim 2, wherein the end effector includes a single spring member located adjacent the pivot.

4. The end effector according to claim 2, wherein the end effector includes two spring members located one on either side of a longitudinal axis of the end effector.

5. The end effector according to claim 1, wherein the at least one spring member is electrically insulating.

6. The end effector according to claim 5, wherein the at least one spring member is formed of an electrically insulating material.

7. The end effector according to claim 6, wherein the at least one spring member is formed of a polymer material.

8. The end effector according to claim 5, wherein the at least one spring member is formed of a metallic material coated with an electrically insulating material.

9. The end effector according to claim 1, wherein the at least one spring member is constrained by a locating structure located on the first member and the second jaw member.

10. The end effector according to claim 9, wherein the locating structure includes recesses located on the first jaw member and the second jaw member.

11. The end effector according to claim 9, wherein the locating structure includes location posts located on the first jaw member and the second jaw member.

12. The end effector according to claim 1, wherein the at least one spring member includes coil springs.

13. The end effector according to claim 1, wherein the at least one spring member includes disc springs.

14. The end effector according to claim 1, wherein the at least one spring member includes leaf springs.

15. An end effector for a surgical instrument, the end effector comprising:

a pair of opposing first and second jaw members, at least one of the first jaw member and the second jaw member being pivotable relative to the other one of the first jaw member and the second member between (i) a first open position in which the first jaw member and the second jaw member are disposed in a spaced relation relative to one another, and (ii) a second closed position in which the first jaw member and the second jaw member cooperate to grasp tissue therebetween, the first jaw member and the second jaw member being configured to be connected to a source of electrical energy such that the first jaw member and the second jaw member conduct energy through the tissue held therebetween to effect a tissue seal; and at least one reactive member connected between the first jaw member and the second jaw member, the first jaw member and the second jaw member moving from the open position to the closed position causing the at least one reactive member to compress, the at least one reactive member having a fully compressed condition in the closed position, the at least one reactive member forming a stop member when the at least one spring member is in the fully compressed condition, the stop member maintaining a predetermined gap distal of the stop member between the first jaw member and the second jaw member along a length of the first jaw member and the second jaw member, when the first jaw member and the second jaw member are in the closed position.

* * * * *